(12) United States Patent
Laas

(10) Patent No.: US 9,567,313 B2
(45) Date of Patent: Feb. 14, 2017

(54) ISOCYANATE-FUNCTIONAL CYCLIC CARBONATES

(71) Applicant: Bayer MaterialScience AG, Leverkusen (DE)

(72) Inventor: Hans-Josef Laas, Odenthal (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 14/424,487

(22) PCT Filed: Aug. 22, 2013

(86) PCT No.: PCT/EP2013/067464
§ 371 (c)(1),
(2) Date: Feb. 27, 2015

(87) PCT Pub. No.: WO2014/033046
PCT Pub. Date: Mar. 6, 2014

(65) Prior Publication Data
US 2015/0225363 A1    Aug. 13, 2015

(30) Foreign Application Priority Data

Aug. 28, 2012 (EP) .................................. 12182067

(51) Int. Cl.
| | | |
|---|---|---|
| *C07D 317/36* | (2006.01) | |
| *C08G 18/28* | (2006.01) | |
| *C07D 319/06* | (2006.01) | |
| *C08G 18/10* | (2006.01) | |
| *C08G 18/32* | (2006.01) | |
| *C08G 18/38* | (2006.01) | |
| *C08G 18/74* | (2006.01) | |

(52) U.S. Cl.
CPC ........... *C07D 319/06* (2013.01); *C07D 317/36* (2013.01); *C08G 18/10* (2013.01); *C08G 18/282* (2013.01); *C08G 18/2815* (2013.01); *C08G 18/3206* (2013.01); *C08G 18/3218* (2013.01); *C08G 18/38* (2013.01); *C08G 18/74* (2013.01)

(58) Field of Classification Search
CPC .. C08G 18/10; C08G 18/18282; C07D 317/36
See application file for complete search history.

(56) References Cited

U.S. PATENT DOCUMENTS

| | | | |
|---|---|---|---|
| 3,072,613 A | 1/1963 | Whelan et al. | |
| 3,084,140 A | 4/1963 | Gurgiolo et al. | |
| 4,835,289 A | 5/1989 | Brindöpke | |
| 5,112,879 A * | 5/1992 | Randall ............... | C08G 18/225 252/182.13 |
| 5,688,891 A | 11/1997 | Hovestadt et al. | |
| 5,861,107 A | 1/1999 | Buysch et al. | |
| 6,428,854 B1 | 8/2002 | Melchiors et al. | |
| 7,790,908 B2 | 9/2010 | Schmitt et al. | |
| 8,118,968 B2 | 2/2012 | Moeller et al. | |
| 2010/0137507 A1 | 6/2010 | Bernard et al. | |

FOREIGN PATENT DOCUMENTS

| | | | | |
|---|---|---|---|---|
| DE | 196 25 265 A1 | 1/1998 | | |
| EP | 0 229 622 A2 | 7/1987 | | |
| EP | 0328150 A2 | 8/1989 | | |
| EP | 0 703 230 A1 | 3/1996 | | |
| EP | 0 739 888 A1 | 10/1996 | | |
| EP | 0 911 352 A2 | 4/1999 | | |
| EP | 1 963 301 A1 | 9/2008 | | |
| WO | WO-02/079292 | * | 10/2002 | ............ C08G 18/76 |
| WO | WO-03016298 A2 | 2/2003 | | |
| WO | WO-2006010408 A1 | 2/2006 | | |
| WO | WO-2008125419 A1 | 10/2008 | | |
| WO | WO-2011159219 A1 | 12/2011 | | |

OTHER PUBLICATIONS

International Search Report for PCT/EP2013/067464 mailed Jan. 2, 2014.

* cited by examiner

*Primary Examiner* — Michael L Leonard
(74) *Attorney, Agent, or Firm* — John E. Mrozinski, Jr.

(57) ABSTRACT

The invention relates to a process for preparing compounds containing isocyanate groups and cyclic carbonate structures, by reacting at least A) a monomeric diisocyanate with aliphatically, cycloaliphatically, araliphatically and/or aromatically bonded isocyanate groups with B) a hydroxyfunctional cyclic carbonate, characterized in that component A) is reacted with component B) in an equivalents ratio of isocyanate groups to hydroxyl groups of at least 8:1. The invention further relates to the products obtainable by the process according to the invention, and to a composition comprising compounds containing isocyanate groups and cyclic carbonate structures. The invention additionally relates to the use of the products obtainable by the process according to the invention and of the composition as a starting component in the preparation of polyurethanes containing cyclic carbonate structures, crosslinkable binders, and also raw materials for coatings, sealants or adhesives.

4 Claims, No Drawings

ISOCYANATE-FUNCTIONAL CYCLIC CARBONATES

CROSS-REFERENCE TO RELATED APPLICATIONS

This application is a national stage application (under 35 U.S.C. §371) of PCT/EP2013/067464, filed Aug. 22, 2013, which claims benefit of European Application No. 12182067.4, filed Aug. 28, 2012, both of which are incorporated herein by reference in their entirety.

The invention relates to a process for preparing compounds containing isocyanate groups and cyclic carbonate structures, to the products obtainable by this process and to a composition comprising compounds containing isocyanate groups and cyclic carbonate structures. The invention further relates to the use of the products obtainable by the process according to the invention and of the inventive composition as a starting component in the preparation of polyurethanes containing cyclic carbonate structures, and in the production of crosslinkable binders and of raw materials for paints, sealants or adhesives.

The reaction of cyclic carbonates with amines to give urethane groups has long been known (e.g. U.S. Pat. No. 3,072,613, U.S. Pat. No. 3,084,140). If compounds having at least two cyclic carbonate groups are combined with polyamines, this reaction can be utilized for formation of polyurethanes.

A very simple, frequently utilized method for preparation of compounds having a plurality of cyclic carbonate groups in the molecule involves the reaction of low molecular weight hydroxy-functional cyclic carbonates with polyisocyanates or isocyanate-functional prepolymers.

For example, WO 2006/010408 describes isocyanate-free reaction products of linear polyurethane prepolymers based on diphenylmethane diisocyanate (MDI) with 4-(hydroxymethyl)-1,3-dioxolan-2-one (glycerol carbonate), which can be crosslinked even at room temperature with compounds bearing at least two primary or secondary amino groups. Such two-component binders find use as adhesives and sealants, especially as laminating adhesive for composite films.

Polyisocyanates blocked with hydroxy-functional cyclic carbonates, for example reaction products of polyisocyanurate polyisocyanates of 1,6-diisocyanatohexane (hexamethylene diisocyanate, HDI) with glycerol carbonate, are provided by WO 2008/125419. Dissolved in specific acetals, such as 1,2-dimethoxyethane in particular, such glycerol carbonate/polyisocyanate adducts with polyether polyamines or polyamide amines likewise cure even at room temperature to give varnish films of high optical quality.

Compounds bearing cyclic carbonate groups can also be combined with hydroxy-functional co-reactants. While the aminic curing of the cyclic carbonate groups proceeds with sufficient speed even at low temperatures, crosslinking in this case, however, takes place only at elevated temperatures, generally under baking conditions, and in the presence of specific catalysts.

EP-A 0 911 352 describes, for example, one-component systems that are storage-stable at room temperature, consisting of polyols, reaction products of polyisocyanurate polyisocyanates of HDI and/or of 1-isocyanato-3,3,5-trimethyl-5-isocyanatomethylcyclohexane (isophorone diisocyanate, IPDI) with 5-(hydroxymethyl)-5-ethyl-1,3-dioxan-2-one (TMP carbonate) as crosslinker components and specific metal carboxylates as curing catalysts, which can be baked at elevated temperatures to give hard solvent-resistant coatings without elimination of volatile compounds.

The preparation of oligourethanes containing 1,3-dioxan-2-one groups from diisocyanates or polyisocyanates using TMP carbonate and the use thereof as crosslinkers for polyols in thermally curable coating systems is also known from EP-A 0 703 230.

The reactive systems that are based on hydroxy-functional cyclic carbonates and are known nowadays are therefore reaction products of such units either with oligomeric polyisocyanates of comparatively low molecular weight or with isocyanate prepolymers of relatively high molecular weight, although these are generally of linear structure. Polyisocyanate components that are of high molecular weight and simultaneously of high functionality have not been described to date as co-reactants for hydroxy-functional cyclocarbonates. However, specifically polymeric polycyclocarbonate polyurethanes of high molecular weight should be of particular interest as binder components since they should react, for example, in combination with the low molecular weight polyamines of good commercial availability, as serve, for example, as crosslinkers for epoxy systems, to give highly crosslinked, particularly stable polyurethanes.

The main cause of the lack of polymeric polycyclocarbonate polyurethanes of high functionality to date is that low-monomer NCO prepolymers of branched polyols of high molecular weight gelate because of the unavoidable onset of crosslinking reactions during the prepolymerization reaction with diisocyanates and the associated increase in molecular weight, or at least have extremely high viscosities that would make them unusable as units for a reaction with hydroxy-functional cyclic carbonates.

The problem addressed by the present invention was therefore that of providing a process for preparing formation components for the synthesis of polyurethanes which have cyclic carbonate structures and are suitable as binders for varnishes and coatings. The formation components obtainable by the process according to the invention shall enable preparation of polyurethanes containing cyclic carbonate structures from any desired polyols, thus also including, for example, highly branched polymeric polyols, in a reliable and reproducible manner.

This object is achieved in accordance with the invention by a process for preparing compounds containing isocyanate groups and cyclic carbonate structures by reaction of at least A) a monomeric diisocyanate having aliphatically, cycloaliphatically, araliphatically and/or aromatically bonded isocyanate groups with B) a hydroxy-functional cyclic carbonate, which is characterized in that component A) is reacted with component B) in a ratio of equivalents of isocyanate groups to hydroxyl groups of at least 8:1.

The process according to the invention is based on the surprising observation that it is possible through reaction of standard hydroxy-functional cyclic carbonates with excess amounts of monomeric diisocyanates in a ratio of equivalents of isocyanate groups to hydroxyl groups of at least 8:1 to obtain compounds which simultaneously have an isocyanate group and a cyclic carbonate group, and with which even highly branched polymeric polyols can be converted without any problem to crystallization-stable polyurethanes having cyclocarbonate end groups. The unconverted monomeric diisocyanates are removed before the further conversion of the compounds.

Compounds containing isocyanate groups and cyclic carbonate structures are basically already known. For example, EP-A 0 328 150 describes the reaction of HDI with glycerol carbonate in organic solution in a ratio of equivalents of isocyanate groups to hydroxyl groups of 6:1 with subsequent distillative removal of the solvent and of the unconverted excess diisocyanate. However, the reaction product obtained was not characterized analytically but processed further directly to give a cyclocarbonate-containing polyester. As shown by in-house studies, however, a very high proportion of the 2:1 bis adduct of glycerol carbonate and HDI, which has a significant tendency to crystallize, forms at the selected ratio of equivalents. The high proportion of bis adduct makes the reaction product of HDI and glycerol carbonate obtainable according to EP 0 328 150 unsuitable as a unit for preparation of polycyclocarbonate polyurethanes that are stable with respect to cloudiness for varnishes and coatings.

The same applies to the compounds formed from diisocyanates and TMP carbonate which contain 1,3-dioxan-2-one groups and are described in EP-A 0 703 230, which can also be prepared using a slight diisocyanate excess up to a ratio of equivalents of isocyanate groups to hydroxyl groups of 2:1. These compounds also have a very high proportion of the non-crystallization-stable 2:1 bis adduct of hydroxy-functional cyclic carbonate and diisocyanate, and they are therefore unsuitable as formation components for polycyclocarbonate polyurethanes.

Compounds which contain isocyanate groups and cyclic carbonate structures and which have been prepared using a smaller excess of diisocyanate than claimed in accordance with the invention and are as described, for example, in EP-A 0 703 230 and EP-A 0 328 150, in contrast to the inventive process products in the case of analogous reaction with polyols, always give turbid polycyclocarbonate polyurethanes unusable as binders for varnishes and coatings.

Starting components B) for the process according to the invention are any desired hydroxy-functional cyclic carbonates of the general formula (I) or mixtures thereof

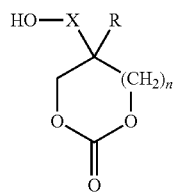

(I)

in which
R is hydrogen or a saturated or unsaturated, linear or branched, aliphatic radical having 1 to 7 carbon atoms,
X is a linear or branched organic radical which has 1 to 36 carbon atoms and which may optionally contain ether, ester and/or carbonate groups, and
n is 0 or 1.

Suitable starting components B) are, for example, simple hydroxy-functional cyclocarbonates, for example 4-(hydroxymethyl)-1,3-dioxolan-2-one (glycerol carbonate), 5-(hydroxymethyl)-5-methyl-1,3-dioxan-2-one and/or 5-(hydroxymethyl)-5-ethyl-1,3-dioxan-2-one (TMP carbonate).

Suitable starting components B) are additionally also the polyether alcohols, polyester alcohols and/or polycarbonate alcohols which have number-average molecular weights of up to 600 g/mol, preferably up to 500 g/mol, more preferably up to 400 g/mol, have cyclic carbonate structures and are obtainable by known methods through reaction of these simple hydroxy-functional cyclic carbonates with alkylene oxides, for example ethylene oxide and/or propylene oxide, lactones, for example β-propiolactone, γ-butyrolactone, δ-valerolactone, ε-caprolactone, 3,5,5- and 3,3,5-trimethylcaprolactone, and/or cyclic carbonates, for example 1,3-dioxan-2-one (trimethylene carbonate) and 5,5-dimethyl-1,3-dioxan-2-one (neopentyl glycol carbonate).

The preparation of the starting compounds B) does not form part of the subject matter of the present application. They can be obtained by known processes, for example using fossil fuels or else from renewable raw materials, for example from biogenic glycerol, as obtained, for example, as a coproduct of biodiesel production.

Examples of possible preparation processes for the abovementioned simple hydroxy-functional cyclic carbonates include reactions of glycerol or trimethylolpropane with ethylene carbonate, dialkyl carbonates or diaryl carbonates, for example dimethyl or diphenyl carbonate, under transesterification conditions (see, for example, EP-A 1 963 301, EP-A 0 739 888, DE-A 196 25 265 and WO2011/159219). In addition, glycerol carbonate can also be obtained by direct reaction of glycidol with carbon dioxide in the presence of suitable catalysts (see, for example, EP-A 0 229 622).

Processes for preparing the compounds which are likewise suitable as starting compounds B) and which additionally contain at least one polyether, polyester and/or polycarbonate group are likewise already known.

For example, the reaction of simple hydroxy-functional cyclic carbonate with alkylene oxides, especially with propylene oxide, by the standard methods for synthesis of polyethers (see, for example, N. Adam et al.: "Polyurethanes", Ullmann's Encyclopedia of Industrial Chemistry, Electronic Release, 7th ed., chap. 3.2.1, Wiley-VCH, Weinheim 2005) in the presence of KOH or especially by the IMPACT process using double metal cyanide (DMC) catalysts gives polyether alcohols which have cyclic carbonate structures in terminal positions and are suitable as starting compound B).

Preferred starting compounds B) having at least one ether group are those of the abovementioned molecular weight range based on glycerol carbonate and propylene oxide.

Suitable starting compounds B) containing at least one ester group as well as a cyclic carbonate group can be prepared in a manner known per se from lactones and the above-described simple hydroxy-functional cyclic carbonates as starter molecules with ring opening. Suitable lactones for preparation of these starting compounds B) containing ester groups are, for example, β-propiolactone, γ-butyrolactone, δ-valerolactone, ε-caproladone, 3,5,5- and 3,3,5-trimethylcaprolactone or any desired mixtures of such lactones.

Preferred starting compounds B) having at least one ester group are those of the abovementioned molecular weight range based on glycerol carbonate and ε-caprolactone.

Finally, likewise suitable as starting compounds B) are also compounds containing at least one further carbonate group as well as a cyclic carbonate group. Compounds of this kind are likewise already known and are obtainable, for example, by the process described in Example 1), Step (A) of WO03/016298 through reaction of the above-described simple hydroxy-functional cyclic carbonates with trimethylene carbonate and/or neopentyl glycol carbonate.

Preferred starting compounds B) having at least one further carbonate group are those of the abovementioned molecular weight range based on glycerol carbonate and neopentyl glycol carbonate.

In general, the above-described starting compounds B) which are suitable for the process according to the invention and contain at least one ester group and/or at least one further carbonate group as well as a cyclic carbonate group are prepared by ring-opening polymerization in the presence of catalysts, for example Lewis or Brønsted acids, organic tin or titanium compounds, at temperatures of 20 to 200° C., preferably 50 to 160° C.

Starting components B) preferred for the process according to the invention are hydroxy-functional cyclic carbonates of the general formula (I), or mixtures thereof, in which
R is hydrogen or a saturated linear aliphatic radical having 1 or 2 carbon atoms,
X is a linear or branched organic radical which has 1 to 18 carbon atoms and which may optionally contain ether, ester and/or carbonate groups, and
n is 0 or 1.

Particularly preferred starting components B) are hydroxy-functional cyclic carbonates of the general formula (I), or mixtures thereof, in which
R is hydrogen or a saturated linear aliphatic radical having 1 or 2 carbon atoms,
X is a methylene group (—CH$_2$—) and
n is 0 or 1.

A very particularly preferred starting component B) is glycerol carbonate.

The hydroxy-functional cyclic carbonates B) can be used in the process according to the invention either individually or in the form of any desired mixtures with one another.

Suitable starting compounds A) for the process according to the invention are any desired diisocyanates which have aliphatically, cycloaliphatically, araliphatically and or aromatically bonded isocyanate groups and can be prepared by any desired processes, for example by phosgenation or by a phosgene-free route, for example by urethane cleavage.

Preferred diisocyanates A) are those of the general formula (II)

OCN—Y—NCO     (II)

in which Y is a linear or branched, aliphatic or cycloaliphatic radical having 4 to 18 carbon atoms or an optionally substituted aromatic or araliphatic radical having 6 to 18 carbon atoms.

Suitable examples are, for example, 1,4-diisocyanatobutane, 1,6-diisocyanatohexane (HDI), 1,5-diisocyanato-2,2-dimethylpentane, 2,2,4- or 2,4,4-trimethyl-1,6-diisocyanatohexane, 1,10-diiisocyanatodecane, 1,3- and 1,4-diisocyanatocyclohexane, 1,4-diisocyanato-3,3,5-trimethylcyclohexane, 1,3-diisocyanato-2-methylcyclohexane, 1,3-diisocyanato-4-methylcyclohexane, 1-isocyanato-3,3,5-trimethyl-5-isocyanatomethylcyclohexane (isophorone diisocyanate; IPDI), 1-isocyanato-1-methyl-4(3)-isocyanatomethylcyclohexane, 2,4'- and 4,4'-diisocyanatodicyclohexylmethane (H$_{12}$-MDI), 1,3- and 1,4-bis(isocyanatomethyl)cyclohexane, 4,4'-diisocyanato-3,3'-dimethyldicyclohexylmethane, 4,4'-diisocyanato-3,3',5,5'-tetramethyldicyclohexylmethane, 4,4'-diisocyanato-1,1'-bi(cyclohexyl), 4,4'-diisocyanato-3,3'-dimethyl-1,1'-bi(cyclohexyl), 4,4'-diisocyanato-2,2',5,5'-tetramethyl-1,1'-bi(cyclohexyl), 1,8-diisocyanato-p-menthane, 1,3-diisocyanatoadamantane, 1,3-dimethyl-5,7-diisocyanatoadamantane, 1,3- and 1,4-bis(isocyanatomethyl)benzene (XDI), 1,3- and 1,4-bis(1-isocyanato-1-methylethyl)benzene (TMXDI), bis(4-(1-isocyanato-1-methylethyl)phenyl) carbonate, phenylene 1,3- and 1,4-diisocyanate, tolylene 2,4- and 2,6-diisocyanate (TDI) and any desired mixtures of these isomers, diphenylmethane 2,4'- and/or 4,4'-diisocyanate (MDI) and naphthylene 1,5-diisocyanate (NDI) and any desired mixtures of such diisocyanates. Further diisocyanates that are likewise suitable can additionally be found, for example, in Justus Liebigs Annalen der Chemie, volume 562 (1949) p. 75-136.

Particularly preferred starting components A) are diisocyanates of the general formula (II) in which Y is a linear or branched, aliphatic or cycloaliphatic radical having 6 to 13 carbon atoms.

Particularly preferred starting components A) for the process according to the invention are 1,6-diisocyanatohexane, 1-isocyanato-3,3,5-trimethyl-5-isocyanatomethylcyclohexane, 2,4'- and/or 4,4'-diisocyanatodicyclohexylmethane or mixtures thereof.

In a preferred embodiment of the process according to the invention, the diisocyanates A) are reacted with at least one hydroxy-functional cyclic carbonate B) at temperatures of 20 to 200° C., preferably 40 to 160° C.

Component A) is reacted with component B) in a ratio of equivalents of isocyanate groups to hydroxyl groups of at least 8:1, preferably at least 10:1 and more preferably at least 12:1.

In a further preferred embodiment of the process according to the invention, component A) is reacted with component B) in a ratio of equivalents of isocyanate groups to hydroxyl groups of not more than 40:1, preferably of not more than 30:1.

The reaction of the starting components A) and B) in the process according to the invention can be executed in solution or without solvent in substance, but is preferably executed without solvent.

The reaction can be conducted without catalysis. The reaction can optionally also be accelerated using customary catalysts known from polyurethane chemistry. Examples include tertiary amines, for example triethylamine, tributylamine, dimethylbenzylamine, diethylbenzylamine, pyridine, methylpyridine, dicyclohexylmethylamine, dimethylcyclohexylamine, N,N,N',N'-tetramethyldiaminodiethyl ether, bis(dimethylaminopropyl)urea, N-methyl- or N-ethylmorpholine, N-cocomorpholine, N-cyclohexylmorpholine, N,N,N',N'-tetramethylethylenediamine, N,N,N',N'-tetramethyl-1,3-butanediamine, N,N,N',N'-tetramethyl-1,6-hexanediamine, pentamethyldiethylenetriamine, N-methylpiperidine, N-dimethylaminoethylpiperidine, N,N'-dimethylpiperazine, N-methyl-N'-dimethylaminopiperazine, 1,2-dimethylimidazole, 2-methylimidazole, N,N-dimethylimidazole-β-phenylethylamine, 1,4-diazabicyclo[2.2.2]octane (DABCO) and bis(N,N-dimethylaminoethyl) adipate, amidines, for example 1,5-diazabicyclo[4.3.0]nonene (DBN), 1,8-diazabicyclo(5.4.0)undec-7-ene (DBU) and 2,3-dimethyl-3,4,5,6-tetrahydropyrimidine, alkanolamine compounds, for example triethanolamine, triisopropanolamine, N-methyldiethanolamine, N-ethyldiethanolamine, dimethylaminoethanol 2-(N,N-dimethylaminoethoxy)ethanol, N,N',N''-tris-(dialkylaminoalkyl)hexahydrotriazine, for example N,N',N''-tris(dimethylaminopropyl)-s-hexahydrotriazine, bis(dimethylaminoethyl) ether and metal salts, for example inorganic and/or organic compounds of iron, lead, bismuth, zinc and/or tin in customary oxidation states of the metal, for example iron(II) chloride, iron(III) chloride, bismuth(III) bismuth(III) 2-ethylhexanoate, bismuth(III) octoate, bismuth(III) neodecanoate, zinc chloride, zinc 2-ethylcaproate, tin(II) octoate, tin(II) ethylcaproate, tin(II) palmitate, dibutyltin(IV) dilaurate (DBTL), dibutyltin(IV) dichloride or lead octoate.

Examples of catalysts for use with preference are tertiary amines, tin compounds, zinc compounds and bismuth compounds of the type specified.

The catalysts mentioned by way of example can be used individually or in the form of any desired mixtures with one another in the preparation of the inventive compounds containing isocyanate groups and cyclic carbonate structures and are used, if at all, in amounts of 0.001% to 1.0% by weight, preferably 0.005% to 0.5% by weight, calculated as the total amount of catalysts used, based on the total amount of starting compounds used.

The progress of the reaction in the process according to the invention can be monitored by determining the NCO content by titrimetric means, for example. On attainment of the desired NCO content, generally after full urethanization, the reaction is stopped.

In a preferred embodiment of the invention, after the reaction of components A) and B), any unconverted excess of monomeric diisocyanates A) is separated from the reaction product apart from a residual content of less than 1% by weight, preferably less than 0.5% by weight, more preferably of less than 0.3% by weight, based on the total mass of the reaction product.

This is preferably done by freeing the reaction mixture of excess monomeric diisocyanates by thin-film distillation under reduced pressure, for example at a pressure of below 1.0 mbar, preferably below 0.5 mbar, more preferably below 0.2 mbar, under very gentle conditions, for example at a temperature of 100 to 200° C., preferably of 120 to 180° C.

The distillates obtained can be used without any problem for a new reaction with suitable starting compounds B).

In a further, although less preferred embodiment of the process according to the invention, the monomeric diisocyanates are separated from the inventive process product formed by extraction with suitable solvents inert toward isocyanate groups, for example aliphatic or cycloaliphatic hydrocarbons such as pentane, hexane, heptane, cyclopentane or cyclohexane.

Irrespective of the type of workup, the products obtained from the process according to the invention are clear, virtually colorless compounds containing isocyanate groups and cyclic carbonate structures, which, depending on the starting diisocyanate chosen, are liquids of low to high viscosity or solid materials and have NCO contents of 4.5% to 14.8% by weight, preferably 5.0% to 14.8% by weight, more preferably 9.0% to 14.5% by weight, and residual contents of monomeric starting diisocyanates of less than 1.0% by weight, preferably of less than 0.5% by weight, more preferably of less than 0.3% by weight, based on the total mass of the reaction product.

The invention further provides compounds containing isocyanate groups and cyclic carbonate structures, obtainable by the process according to the invention.

The invention likewise provides a composition comprising a) compounds of the general formula (III) containing isocyanate groups and cyclic carbonate structures,

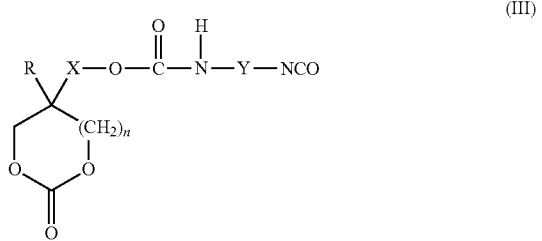

(III)

b) compounds of the general formula (IV) containing two cyclic carbonate structures

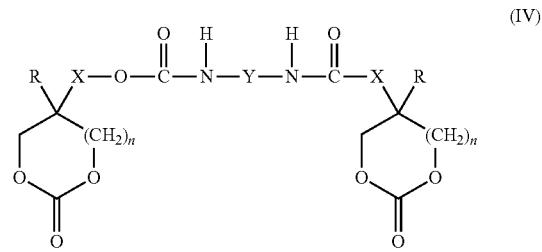

(IV)

and c) monomeric diisocyanates having aliphatically, cycloaliphatically, araliphatically and/or aromatically bonded isocyanate groups, where, in the formulae (III) and (IV), R is hydrogen or a saturated or unsaturated, linear or branched, aliphatic radical having 1 to 7 carbon atoms, X is a linear or branched organic radical which has 1 to 36 carbon atoms and which may optionally contain ether, ester and/or carbonate groups, n is 0 or 1 and Y is a linear or branched, aliphatic or cycloaliphatic radical having 4 to 18 carbon atoms or an optionally substituted aromatic or araliphatic radical having 6 to 18 carbon atoms, characterized in that, based in each case on the total amount of components a) and b), component a) makes up a proportion of ≥88% by weight, preferably ≥90% by weight, more preferably ≥92% by weight, and component b) a proportion of ≤12% by weight, preferably ≤10% by weight, more preferably ≤8% by weight, and component c) is present to an extent of ≤1% by weight, in the overall composition.

In a preferred embodiment of the invention, component b) makes up a proportion of 0.5% to 12% by weight, preferably 0.5% to 10% by weight, more preferably of 0.5% to 8% by weight, based on the total amount of components a) and b).

Preferred inventive compositions are those in which, in the formulae (III) and (IV), R is hydrogen or a saturated linear aliphatic radical having 1 or 2 carbon atoms, X is a linear or branched organic radical which has 1 to 18 carbon atoms and which may optionally contain ether, ester and/or carbonate groups, and n is 0 or 1.

Particularly preferred inventive compositions are those in which, in the formulae (III) and (IV), R is hydrogen or a saturated linear aliphatic radical having 1 or 2 carbon atoms, X is a methylene group (—CH$_2$—) and n is 0 or 1.

Likewise preferred inventive compositions are those in which, in the formulae (III) and (IV), Y is a linear or branched, aliphatic or cycloaliphatic radical having 6 to 13 carbon atoms.

The preferred embodiments specified above for starting component A) likewise apply to the monomeric diisocyanates c).

The invention especially also provides for the use of the inventive compounds containing isocyanate groups and cyclic carbonate structures or of the inventive composition of compounds containing isocyanate groups and cyclic carbonate structures as starting components in the preparation of polyurethanes containing cyclic carbonate structures, or in the production of crosslinkable binders and of crosslinkable raw materials for varnishes, sealants or adhesives. The polyurethanes containing cyclic carbonate structures or crosslinkable binders are preferably used for production of raw materials for varnishes, sealants or adhesives.

The invention further provides polyurethanes containing cyclic carbonate structures, prepared using the inventive compounds containing isocyanate groups and cyclic carbonate structures or the inventive composition of compounds containing isocyanate groups and cyclic carbonate structures.

These can be prepared by reacting the inventive compounds containing isocyanate groups and cyclic carbonate structures or the inventive composition of compounds containing isocyanate groups and cyclic carbonate structures with any desired polyols, preferably at least difunctional polyols, for example simple polyhydric alcohols, ether alcohols or ester alcohols, or standard polymeric polyether polyols, polyester polyols, polycarbonate polyols and/or polyacrylate polyols known from polyurethane chemistry.

EXAMPLES

The invention is illustrated in detail hereinafter by examples.

All percentages are based on weight, unless stated otherwise.

The NCO contents were determined by titrimetric means to DIN EN ISO 11909.

OH numbers were determined by titrimetric means to DIN 53240-2: 2007-11.

The residual monomer contents were measured by gas chromatography to DIN EN ISO 10283.

The proportions of bis adduct (formed from two molecules of hydroxy-functional cyclic carbonate and one molecule of diisocyanate) were determined by gel permeation chromatography based on DIN 55672-1 (Gel permeation chromatography (GPC)—Part 1: Tetrahydrofuran (THF) as elution solvent) at room temperature, with the alteration that a flow rate of 0.6 ml/min rather than 1.0 ml/min was employed. The proportions of bis adduct in area % taken from the chromatograms, which were determined with software support, were each equated approximately to proportions in % by weight and reported as such, based on the total amount of mono adduct and bis adduct.

All the viscosity measurements were made with a Physica MCR 51 rheometer from Anton Paar Germany GmbH (DE) to DIN EN ISO 3219.

The melting ranges reported were determined to ANSI/ASTM D 3451-76 with the aid of a Kofler hot bench from Wagner & Munz GmbH (DE).

Example 1

Inventive 1344 g (8 mol) of hexamethylene diisocyanate (HDI) were initially charged under dry nitrogen at a temperature of 100° C., 118 g (1 mol) of glycerol carbonate was added within 30 minutes and the mixture was stirred for a further 5 hours until an NCO content of 43.1%, corresponding to full urethanization, had been attained. Subsequently, the unconverted monomeric HDI was removed on a thin-film evaporator at a temperature of 140° C. and a pressure of 0.1 mbar. This gave a virtually colorless, clear isocyanate-functional cyclic carbonate which gradually crystallized through at room temperature within one week.

The product had the following characteristic data:
NCO content: 14.0%
Monomeric HDI: 0.18%
Melting range: 28-30° C.
Proportion of bis adduct: 4.6%

Example 2

Inventive

By the process described in example 1, 1008 g (6 mol) of HDI were reacted with 118 g (1 mol) of glycerol carbonate. On attainment of an NCO content of 41.0%, corresponding to full urethanization, the unconverted monomeric HDI was removed by thin-film distillation as described in example 1, and a clear, virtually colorless isocyanate-functional cyclic carbonate was obtained, which gradually crystallized through at room temperature within one week.

The product had the following characteristic data:
NCO content: 14.0%
Monomeric HDI: 0.18%
Melting range: 28-30° C.
Proportion of bis adduct: 6.1%

Example 3

Inventive

By the process described in example 1, 1680 g (10 mol) of HDI were reacted with 118 g (1 mol) of glycerol carbonate. On attainment of an NCO content of 44.4%, corresponding to full urethanization, the unconverted monomeric HDI was removed by thin-film distillation as described in example 1, and a clear, virtually colorless isocyanate-functional cyclic carbonate was obtained, which gradually crystallized through at room temperature within one week.

The product had the following characteristic data:
NCO content: 14.1%
Monomeric HDI: 0.19%
Melting range: 28-30° C.
Proportion of bis adduct: 3.8%

Example 4

Inventive

By the process described in example 1, 1680 g (10 mol) of HDI were reacted with 59 g (0.5 mol) of glycerol carbonate. On attainment of an NCO content of 45.9%, corresponding to full urethanization, the unconverted monomeric HDI was removed by thin-film distillation as described in example 1, and a clear, virtually colorless isocyanate-functional cyclic carbonate was obtained, which gradually crystallized through at room temperature within one week.

The product had the following characteristic data:
NCO content: 14.4%
Monomeric HDI: 0.09%
Melting range: 29-31° C.
Proportion of bis adduct: 1.9%

Example 5

Inventive

By the process described in example 1, 672 g (4 mol) of HDI were reacted with 118 g (1 mol) of glycerol carbonate.

On attainment of an NCO content of 37.2%, corresponding to full urethanization, the unconverted monomeric HDI was removed by thin-film distillation as described in example 1, and a clear, virtually colorless isocyanate-functional cyclic carbonate was obtained, which gradually crystallized through at room temperature within one week.

The product had the following characteristic data:
NCO content: 13.4%
Monomeric HDI: 0.11%
Melting range: 27-30° C.
Proportion of bis adduct: 9.1%

Example 6

Inventive

By the process described in example 1, 1776 g (8 mol) of isophorone diisocyanate (IPDI) were reacted with 118 g (1 mol) of glycerol carbonate. On attainment of an NCO content of 33.3%, corresponding to full urethanization, the unconverted monomeric IPDI was removed by thin-film distillation at a temperature of 160° C. and a pressure of 0.2 mbar, and an isocyanate-functional cyclic carbonate was obtained in the form of a clear, pale yellow solid resin.
NCO content:
Monomeric IPDI: 0.21%
Proportion of bis adduct: 4.5%

Example 7

Inventive

By the process described in example 1, 2096 g (8 mol) of 4,4'-diisocyanatodicyclohexylmethane ($H_{12}$-MDI) were reacted with 118 g (1 mol) of glycerol carbonate. On attainment of an NCO content of 28.5%, corresponding to full urethanization, the unconverted monomeric $H_{12}$-MDI was removed by thin-film distillation at a temperature of 170° C. and a pressure of 0.2 mbar, and an isocyanate-functional cyclic carbonate was obtained in the form of a clear, pale yellow solid resin.
NCO content: 10.3%
Monomeric $H_{12}$-MDI: 0.28%
Proportion of bis adduct: 4.6%

Example 8

Inventive

By the process described in example 1, 1344 g (8 mol) of HDI were reacted with 160 g (1 mol) of TMP carbonate. On attainment of an NCO content of 41.9%, corresponding to full urethanization, the unconverted monomeric HDI was removed by thin-film distillation as described in example 1, and a clear, colorless isocyanate-functional cyclic carbonate was obtained with the following characteristic data:
NCO content: 12.1%
Monomeric HDI: 0.17%
Viscosity (23° C.): 77 000 mPas
Proportion of bis adduct: 5.1%

Example 9

Inventive 118 g (1 mol) of glycerol carbonate and 114 g (1 mol) of ε-caprolactone were mixed at room temperature under dry nitrogen, 0.02 g of ortho-phosphoric acid was added and then the mixture was heated to 160° C. for 5 h. After cooling to room temperature, a colorless polyester alcohol having terminal cyclic carbonate structures was present with the following characteristic data:
OH number: 244 mg KOH/g
Free ε-caprolactone: 0.15%
Viscosity (23° C.): 2950 mPas
Mean molecular weight (calc. from OH number); 230

230 g (1.0 mol) of this glycerol carbonate/ε-caprolactone adduct were reacted with 1344 g (8 mol) of HDI by the process described in example 1. On attainment of an NCO content of 40.0%, corresponding to full urethanization, the unconverted monomeric HDI was removed by thin-film distillation as described in example 1, and a clear, virtually colorless isocyanate-functional cyclic carbonate having ester groups was obtained with the following characteristic data:
NCO content: 9.8%
Monomeric HDI: 0.19%
Viscosity (23° C.): 3100 mPas
Proportion of bis adduct: 5.3%

Example 10

Comparative

By the process described in example 1, 504 g (3 mol) of HDI were reacted with 118 g (1 mol) of glycerol carbonate. On attainment of an NCO content of 33.8%, corresponding to full urethanization, the unconverted monomeric HDI was removed by thin-film distillation as described in example 1, and a clear, virtually colorless isocyanate-functional cyclic carbonate was obtained, which partly crystallized after being cooled to room temperature.

The product had the following characteristic data:
NCO content: 12.7%
Monomeric HDI: 0.19%
Proportion of bis adduct: 13.5%

Example 11

Use, Inventive 270 g (0.9 mol) of the isocyanate-functional cyclic carbonate from example 1 were initially charged under dry nitrogen in 207 g of tetramethoxyethane as solvent at a temperature of 80° C., 40 g (0.3 mol) of trimethylolpropane (TMP) were added in portions within 20 min, and the mixture was stirred for a further 4 hours until the isocyanate band in the IR spectrum disappeared completely. The 60% clear solution of a polyurethane bearing terminal cyclocarbonate groups that was present had a viscosity of 5540 mPas at 23° C.

Example 12

Comparative

To 1680 g (10 mol) of HDI at a temperature of 80° C. under dry nitrogen were added 134 g (1 mol) of TMP within one hour, and the mixture was stirred for one further hour until an NCO content of 39.4%, corresponding to full urethanization, had been attained. Subsequently, the unconverted monomeric HDI was removed on a thin-layer evaporator at a temperature of 130° C. and a pressure of 0.1 mbar. This gave a colorless clear polyisocyanate having an NCO content of 16.7%, a content of monomeric HDI of 0.21% and a viscosity (23° C.) of 480 000 mPas.

251 g (1.0 eq) of this high-viscosity polyisocyanate were dissolved in 246 g of tetramethoxyethane under dry nitrogen, then 118 g (1.0 mol) of glycerol carbonate were added at a temperature of 80° C. and the mixture was stirred for a further 5 hours until the isocyanate band in the IR spectrum disappeared completely. The 60% solution of a polyurethane bearing terminal cyclocarbonate groups that was present had a viscosity of 12 360 mPas at 23° C.

Compared to the reaction product of an inventive isocyanate-functional cyclic carbonate with TMP obtained according to example 11, the reaction product of a hydroxy-functional cyclic carbonate with a low-monomer isocyanate prepolymer based on TMP prepared according to example 12 exhibits a much lower viscosity, even though the two polyurethanes are based on the same starting components.

Example 13

Use, Inventive 282 g (0.9 mol) of the isocyanate-functional cyclic carbonate from example 5 were initially charged under dry nitrogen in 215 g of tetramethoxyethane as solvent at a temperature of 80° C., 40 g (0.3 mol) of trimethylolpropane (TMP) were added in portions within 20 min, and the mixture was stirred for a further 4 hours until the isocyanate band in the IR spectrum disappeared completely. The 60% clear solution of a polyurethane bearing terminal cyclocarbonate groups that was present had a viscosity of 5220 mPas at 23° C.

Example 14

Use, Comparative 298 g (0.9 mol) of the noninventive isocyanate-functional cyclic carbonate from example 10 were initially charged under dry nitrogen in 225 g of tetramethoxyethane as solvent at a temperature of 80° C., 40 g (0.3 mol) of trimethylolpropane (TMP) were added in portions within 20 min, and the mixture was stirred for a further 4 hours until the isocyanate band in the IR spectrum disappeared completely. The 60% solution of a polyurethane bearing terminal cyclocarbonate groups that was present turned very cloudy immediately after being cooled down to room temperature and formed a conspicuous sediment within one day.

Comparison with the reaction product of the inventive isocyanate-functional cyclic carbonate from example 1) with TMP, obtained as a clear solution according to example 13), shows that the isocyanate-functional cyclic carbonate from example 10), which was prepared using a smaller excess of isocyanate groups than the minimum according to the invention, is not crystallization-stable because of an excessively high proportion of bis adduct and hence is unsuitable for preparation of polyurethanes bearing cyclocarbonate groups.

The invention claimed is:
1. A composition comprising
a) a compound of the general formula (III) containing an isocyanate group and a cyclic carbonate structure,

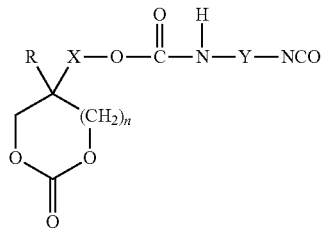

b) a compound of the general formula (IV) containing cyclic carbonate structures,

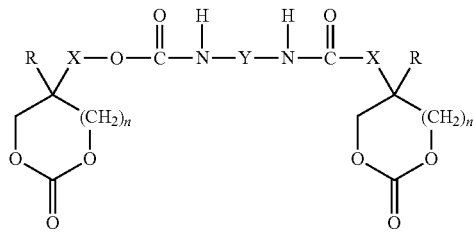

and
c) a monomeric diisocyanate having aliphatically, cycloaliphatically, araliphatically and/or aromatically bonded isocyanate groups,
where, in the formulae (III) and (IV),
R is hydrogen or a saturated or unsaturated, linear or branched, aliphatic radical having 1 to 7 carbon atoms,
X is a linear or branched organic radical which has 1 to 36 carbon atoms and which may optionally contain ether, ester and/or carbonate groups,
n is 0 or 1 and
Y is a linear or branched, aliphatic or cycloaliphatic radical having 4 to 18 carbon atoms or an optionally substituted aromatic or araliphatic radical having 6 to 18 carbon atoms,
wherein, based in each case on the total amount of components a) and b), component a) makes up a proportion of ≥88% by weight, and component b) a proportion of ≤12% by weight, and component c) is present to an extent of ≤1% by weight, in the overall composition.

2. The composition as claimed in claim 1, wherein component b) makes up a proportion of 0.5% to 12% by weight, based on the total amount of components a) and b).

3. A method comprising utilizing the composition as claimed in claim 1 as a starting component in the production of polyurethanes containing cyclic carbonate structures or as a starting component in the production of crosslinkable binders or as a starting component in the production of crosslinkable raw materials for varnishes, sealants or adhesives.

4. A polyurethane containing cyclic carbonate structures, prepared using the composition containing isocyanate groups and cyclic carbonate structures as claimed in claim 1.

* * * * *